United States Patent [19]

Reed, Jr.

[11] 3,968,150
[45] July 6, 1976

[54] PROCESS FOR THE PREPARATION OF NITROGEN- AND FLUORINE-CONTAINING ACRYLATES AND METHACRYLATES

[75] Inventor: Samuel F. Reed, Jr., Huntsville, Ala.

[73] Assignee: Rohm and Haas Company, Philadelphia, Pa.

[22] Filed: Apr. 13, 1964

[21] Appl. No.: 360,168

[52] U.S. Cl............................... 260/486 D; 149/44; 149/109.4
[51] Int. Cl.².......................................... C07C 69/54
[58] Field of Search.................. 260/482, 486, 486 D Primary Examiner—Leland A. Sebastian

EXEMPLARY CLAIM

1. A method for the preparation of difluoraminoalkyl acrylates and methacrylates in which there are at least two difluoramino groups present and the alkyl contains two to eighteen carbon atoms which comprises reacting in the temperature range of about 0° C. up to the reflux temperature of the reaction mixture a member from the class consisting of a difluoraminoalkyl α,β-dibromopropionate and difluoraminoalkyl α,β-dibromoisobutyrate in the presence of a compound having the formula

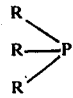

wherein R is a member from the group consisting of alkoxy one to four carbon atoms, alkyl one to eight carbon atoms, phenyl, alkylphenyl in which the alkyl portion contains from one to eight carbon atoms, phenoxy and alkylphenoxy in which the alkyl portion contains from one to eight carbon atoms.

12 Claims, No Drawings

PROCESS FOR THE PREPARATION OF NITROGEN- AND FLUORINE-CONTAINING ACRYLATES AND METHACRYLATES

This invention concerns a process for the preparation of difluoraminoalkyl acrylates and methacrylates, in which there are at least two difluoramino groups present and the alkyl portion contains two to eighteen carbon atoms.

The process of this invention involves the reaction of difluoraminoalkyl α,β-dibromopropionates or isobutyrates, in which the alkyl portion contains from two to eighteen carbon atoms, preferably two to twelve carbon atoms, in the presence of a compound having the formula

The symbol R represents an alkoxy group of one to four carbon atoms, an alkyl group of one to eight carbon atoms, a phenyl group, an alkylphenyl group in which the alkyl portion contains from one to eight carbon atoms, a phenoxy group or an alkylphenoxy group in which the alkyl portion contains from one to eight carbon atoms. Within the above definitions of the symbol R, alkyl may have any of its known structural configurations such as normal, iso-, and tertiary. The alkyl substitution on the phenyl ring may be in the form of one or more alkyl groups so long as the total carbon content is adhered to.

Typical embodiments of the propionate and isobutyrate reactants include:

bis(difluoramino)ethyl α,β-dibromopropionate
bix(difluoramino)propyl α,β-dibromopropionate
bis(difluoramino)butyl α,β-dibromopropionate
bis(difluoramino)hexyl α,β-dibromopropionate
bis(difluoramino)dodecyl α,β-dibromopropionate
bis(difluoramino)octadecyl α,β-dibromopropionate
bis(difluoramino)ethyl α,β-dibromoisobutyrate
bis(difluoramino)propyl α,β-dibromoisobutyrate
bis(difluoramino)butyl α,β-dibromoisobutyrate
bis(difluoramino)hexyl α,β-dibromoisobutyrate
bis(difluoramino)dodecyl α,β-dibromoisobutyrate
bis(difluoramino)octadecyl α,β-dibromoisobutyrate tetrakis(difluoramino)butyl α,β-dibromopropionate
tetrakis(difluoramino)amyl α,β-dibromopropionate
tetrakis(difluoramino)hexyl α,β-dibromopropionate
tetrakis(difluoramino)octyl α,β-dibromopropionate
tetrakis(difluoramino)dodecyl α,β-dibromopropionate
tetrakis(difluoramino)octadecyl α,β-dibromopropionate
tetrakis(difluoramino)butyl α,β-dibromoisobutyrate
tetrakis(difluoramino)amyl α,β-dibromoisobutyrate
tetrakis(difluoramino)hexyl α,β-dibromoisobutyrate
tetrakis(difluoramino)octyl α,β-dibromoisobutyrate
tetrakis(difluoramino)dodecyl α,β-dibromoisobutyrate
tetrakis(difluoramino)octadecyl α,β-dibromoisobutyrate The difluoramino groups in the above reactants are positioned within the alcohol moiety of the compound and paired on vicinal carbon atoms.

These reactants are themselves prepared by reacting an alkenyl α,β-dibromopropionate or isobutyrate with tetrafluorohydrazine at a temperature of about 50° C. to 120° C. or by reacting the corresponding alkyl ester with tetrafluorohydrazine at elevated temperatures of about 200° to 400° C. Also, some of the reactants may be prepared by using the corresponding anhydride or acid chloride in place of the ester, and reacting with a carbinol having the formula

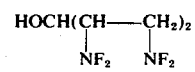

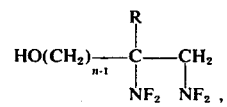

in which n is an integer of one to twelve and R is hydrogen or methyl. The ethyl ester reactants are prepared by reacting vinyl acetate with isobutyric or propionic acid to form the vinyl ester followed by reaction with tetrafluorohydrazine.

Typical embodiments of the compound having the formula

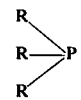

include those wherein R represents methoxy, ethoxy, isopropoxy, butyloxy, phenyl, phenoxy, methylphenoxy, ethylphenoxy, butylphenoxy, methylphenyl, ethylphenyl, dimethylphenyl, dibutylphenyl, ethyl isopropyl, tert-butyl, hexyl and octyl. The preferred embodiments are those in which R represents alkoxy, phenyl, or alkylphenyl groups. Particularly advantageous are those in which R represents phenyl or alkylphenyl in that higher yields of desired product are obtained at lower reaction temperatures and separation of the product is more readily achieved. It is preferred to use the phosphorus reactant in some excess up to about two equivalents per equivalent of the ester reactant.

The reaction is conducted in the presence of an inert volatile organic solvent preferably one that is a solvent for both the desired product as well as the phosphorus containing reactant. There may advantageously be employed aromatic and aliphatic hydrocarbons, chlorinated hydrocarbons, ethers and ketones. Typical embodiments of the solvents include diethyl ether, dipropyl ether, pentane, hexane, chloroform, carbon tetrachloride, methylene chloride, benzene, toluene, xylene and acetone. It is preferred to use the lower boiling solvents in order to make isolation of the desired product more convenient.

The reaction is conducted in a temperature range from about 0° C. up to the reflux temperature of the reaction system, the preferred range being from about 25° C. to about 80° C. The lower reaction temperatures have been more advantageously employed when the symbol R in the phosphorus reactant represents phenyl or alkylphenyl. It is desirable to employ the lower reaction temperatures since the products are known high energy compounds. Furthermore, when R represents phenyl or alkylphenyl, the dibromide of the phosphorus reactant which forms during the course of the reaction precipitates from the reaction solution, thereby facilitating the separation of the product.

Separation of the product is no particular problem if it is distillable at temperatures of up to about 50° C. at reduced pressures, for instance, at about 5 to 10 mm. of mercury or less. However, when the product is heavy and not readily distillable at the conditions just mentioned, then it is particularly preferred to employ a phosphorus reactant that will precipitate from the reaction solution as the reaction progresses and finally terminates.

The products are known (difluoramino)alkyl acrylates and methacrylates containing at least two difluoramino groups. The former resulting when a propionate reactant is employed and the latter resulting when an isobutyrate is used. The compounds are homopolymerizable and copolymerizable with other ethylenically unsaturated monomers. These products have known uses as high energy binders in propellant systems where they are generally employed in the range of about 10 to 30% by weight in a system consisting of a plasticizer for the acrylate or methacrylate, ammonium perchlorate and aluminum.

The present invention may be more fully understood from the following examples which are offered by way of illustration and not by way of limitation. Parts by weight are used throughout.

EXAMPLE I

Preparation of 2,3-bis(difluoramino)propyl acrylate

To a 200 ml. three-necked flask fitted with mechanical stirrer, condenser, thermometer and dropping funnel (all outlets covered with Drierite drying tubes) is introduced 7.72 parts (0.029 mole) of triphenylphosphine and 100 ml. anhydrous diethyl ether (commercial grade). To this solution is added 11.0 parts (0.029 mole) of 2,3-bis(difluoramino)propyl $\alpha,\beta$-dibromopropionate. A slightly exothermic heat of reaction (23° C. to 27° C.) and an immediate precipitate of triphenylphosphine dibromide are noted. The addition is completed within a 10-minute period. The reaction is continued for a period of 24 hours. The solids are removed by filtration and the ether at reduced pressure on a rotary evaporator. The residue, containing a small quantity of solids, is treated with 100 ml. of pentane and filtered again. The pentane is removed and the residue first examined by gas chromatography and then distilled. The gas chromatogram showed the product to be approximately 95 percent pure. The product (b.p. 52° C. 1.1 mm. of mercury) is obtained in a yield of 4.22 parts (67 percent). The infrared spectrum of the product is identical in every respect to that of known 2,3-bis(difluoramino)propyl acrylate. The product gives the following analysis:

Calc'd for $C_6H_8F_4N_2O_2$: %C, 33.33; %H, 3.70; %F, 35.19; %N, 12.96.

Found: %C, 33.25; %H, 4.42; %F, 35.1; %N, 14.35.

EXAMPLE II

Preparation of 2,3-bis(difluoramino)propyl acrylate

Employing a system similar to that of Example 1, 7.30 parts (0.044 mole) of triethylphosphite is added to a solution of 16.5 parts (0.044 mole) of 2,3-bis(difluoramino)-propyl $\alpha,\beta$-dibromopropionate in 100 ml. of dry benzene. The addition is made over a period of 30 minutes. A slightly exothermic reaction (25° to 36° C.) is observed. The mixture is stirred at ambient temperature for 24 hours, freed of solvent and distilled to give 2.89 parts (30 percent) of 2,3-bis(difluoramino)-propyl acrylate (b.p. 42° C., 0.45 mm. of mercury). The product conforms to the known 2,3-bis(difluoramino)propyl acrylate. The product gives the following analysis:

Calc'd for $C_6H_8F_4N_2O_2$: %C, 33.19; %H, 3.70; %F, 35.19; %N, 12.96.

Found: %C, 33.42; %H, 3.81; %F, 36.90; %N, 14.00.

EXAMPLE III

Preparation of 1,2-bis(difluoramino)ethyl methacrylate

Employing a system similar to that used in Example I, 20.8 parts (0.055 mole) 1,2-bis(difluoramino)ethyl $\alpha,\beta$-dibromoisobutyrate is added over a period of thirty minutes to 14.45 parts (0.055 mole) triphenylphosphine in 200 ml. of anhydrous diethyl ether to give an immediate precipitate of triphenylphosphine dibromide. Another 100 ml. of anhydrous ether is added during the course of the addition to facilitate stirring of the mixture. After 18 hours the mixture is filtered free of solids followed by removal of the ether at reduced pressure on a rotary evaporator. The residue when examined by gas chromatography is found to be 97–98 percent pure. Distillation of the residue gives 7.5 parts (63 percent) of 1,2-bis(difluoramino)ethyl methacrylate (b.p. 50° C/5.5 mm. of mercury), $n_D^{20}$ 1.3944. Identification is based on infrared spectral data and elemental analysis. The product conforms to the known 1,2-bis(difluoramino)-ethyl methacrylate. The product gives the following analysis:

Calc'd for $C_6H_8F_4N_2O_2$:
%C, 33.19; %H, 3.70; %F, 35.19; %N, 12.96.
Found: %C, 33.95; %H, 4.81; %F, 36.10; %N, 12.71.

TABLE I

The procedure of Example I is employed in the following examples:

| Ex. No. | R—P R (g.) | Ester Reactant (g.) | Solvent (ml.) | Temp. During Addition (°C.) | Time of Reaction (hrs.) | Product | Yield (g.-%) | Means of Purifin |
|---|---|---|---|---|---|---|---|---|
| IV | Triphenyl phosphine $\phi_3P$ (7.58) | 3(1,2,4,5-tetrakis(difluoramino)amyl)-$\alpha,\beta$-dibromopropionate(12.5) | Pentane (300) | 23–27 | 20 | 3-(1,2,4,5-tetrakis(difluoramino) amyl) acrylate | 5.5–64 | Column chromatography over silica gel** |
| | | | | | **Eluted by 60/40 mixture of carbon tetrachloride/chloroform | | | |
| V | Triphenyl phosphine $\phi_3P$ (28.93) | 3(1,2,4,5-tetrakis(difluoramino)amyl)-$\alpha,\beta$-dibromoisobutyrate(28.0) | Diethyl ether (300) | <25 | 60 | 3-(1,2,4,5-tetrakis(difluoramino) amyl) methacrylate | 10:0–52 | SAME |
| VI | Triphenyl | 3-(1,2,4,5-(difluoramino) | Diethyl | | | 3-(1,2,5,6-tetrakis- | | |

TABLE I-continued

The procedure of Example I is employed in the following examples:

| Ex. No. | R₃P (g.) | Ester Reactant (g.) | Solvent (ml.) | Temp. During Addition (°C.) | Time of Reaction (hrs.) | Product | Yield (g.-%) | Means of Purifin |
|---|---|---|---|---|---|---|---|---|
|  | phosphine φ₃P (20.96) | hexyl)-α,β-dibromopropion- ate (25.0) | ether (400) | 15-20 | 2 | (difluoramino)hexyl) acrylate | 12.0-71 | SAME |
| VII | Triphenyl phosphine φ₃P (26.3) | 3-(1,2,5,6-tetrakis- (difluoramino)hexyl) α,β-dibromoisobutyrate (26.7) | Diethyl ether (300) | <25 | 20 | 3-(1,2,5,6-tetrakis- (difluoramino)hexyl) methacrylate | 15.5-83 | SAME |

TABLE II

| REACTION PRODUCT | $N_D^{20}$ | % C | % H | % F | % N |
|---|---|---|---|---|---|
| IV | — | 27.76/27.69 | 2.91/3.03 | 43.90/44.6 | 16.18/15.99 |
| V | 1.4131 | 30.00/30.70 | 3.36/3.73 | 42.20/44.7 | 15.55/15.40 |
| VI | 1.4187 | 30.00/28.97 | 3.36/3.64 | 42.20/41.4 | 15.55/15.70 |
| VII | 1.4201 | 32.09/32.05 | 3.77/3.80 | 40.62/38.6 | 14.96/14.53 |

Products were also characterized by their infrared spectra.
Elemental analysis (calculated/found).

I claim:

1. A method for the preparation of difluoraminoalkyl acrylates and methacrylates in which there are at least two difluoramino groups present and the alkyl contains two to eighteen carbon atoms which comprises reacting in the temperature range of about 0° C. up to the reflux temperature of the reaction mixture a member from the class consisting of a difluoraminoalkyl α,β-dibromopropionate and difluoraminoalkyl α,β-dibromoisobutyrate in the presence of a compound having the formula

wherein R is a member from the group consisting of alkoxy one to four carbon atoms, alkyl one to eight carbon atoms, phenyl, alkylphenyl in which the alkyl portion contains from one to eight carbon atoms, phenoxy and alkylphenoxy in which the alkyl portion contains from one to eight carbon atoms.

2. A process according to claim 1 wherein the reaction is conducted in the range of about 25° C. to about 80° C.

3. A process according to claim 1 wherein the reaction is conducted in the presence of an inert volatile organic solvent and the phosphorus-containing compound is used in excess.

4. A process according to claim 1 wherein R represents phenyl.

5. A process according to claim 1 wherein R represents alkylphenyl.

6. A process according to claim 1 wherein R represents alkoxy.

7. A process according to claim 1 wherein acrylates are produced.

8. A process according to claim 1 wherein methacrylates are produced.

9. A process according to claim 7 in which there are present in the product two difluoramino groups.

10. A process according to claim 7 in which there are present in the product four difluoramino groups.

11. A process according to claim 8 in which there are present in the product two difluoramino groups.

12. A process according to claim 8 in which there are present in the product four difluoramino groups.

* * * * *